United States Patent [19]

Hadler et al.

[11] 4,035,505

[45] July 12, 1977

[54] 4-HYDROXYCOUMARIN COMPOUNDS USEFUL AS ANTICOAGULANT RODENTICIDES

[75] Inventors: Malcolm Ronald Hadler, Tapporley, England; Roy Stanley Shadbolt, deceased, late of Westminster Park, England, by Elizabeth Godsmark Shadbolt, administratix

[73] Assignee: Ward Blenkinsop and Company Limited, Wembley, England

[21] Appl. No.: 650,720

[22] Filed: Jan. 20, 1976

Related U.S. Application Data

[62] Division of Ser. No. 473,161, May 22, 1974, Pat. No. 3,957,824.

[30] Foreign Application Priority Data

| | | |
|---|---|---|
| May 23, 1973 | United Kingdom | 24685/73 |
| May 25, 1973 | United Kingdom | 25264/73 |
| Mar. 1, 1974 | United Kingdom | 9450/74 |

[51] Int. Cl.$^2$ .................................... A01N 9/28
[52] U.S. Cl. ............................................ 424/281
[58] Field of Search .............. 424/281; 260/343.2 R

[56] References Cited

U.S. PATENT DOCUMENTS

| | | | |
|---|---|---|---|
| 2,872,457 | 2/1959 | Schroeder et al. | 260/343.2 |
| 2,952,689 | 9/1960 | Enders et al. | 260/343.2 |

OTHER PUBLICATIONS

Weygand Preparative Organic Chem. (1972), p. 222.

*Primary Examiner*—Allen J. Robinson
*Attorney, Agent, or Firm*—Wenderoth, Lind & Ponack

[57] ABSTRACT

Novel 4-hydroxy coumarins substituted in the 3 position with substituted tetrahydronaphthyl groups are described. A method of making them by condensing 4-hydroxy coumarin with hydroxyl or halogeno derivatives of the substituted tetrahydronaphthalenes is described. The compounds of the invention are potent anticoagulants finding typical uses as rodenticides. As rodenticides they are particularly effective against rodents resistant to such agents as Warfarin, Coumatetralyl, Diphacinone and Pival.

14 Claims, 1 Drawing Figure

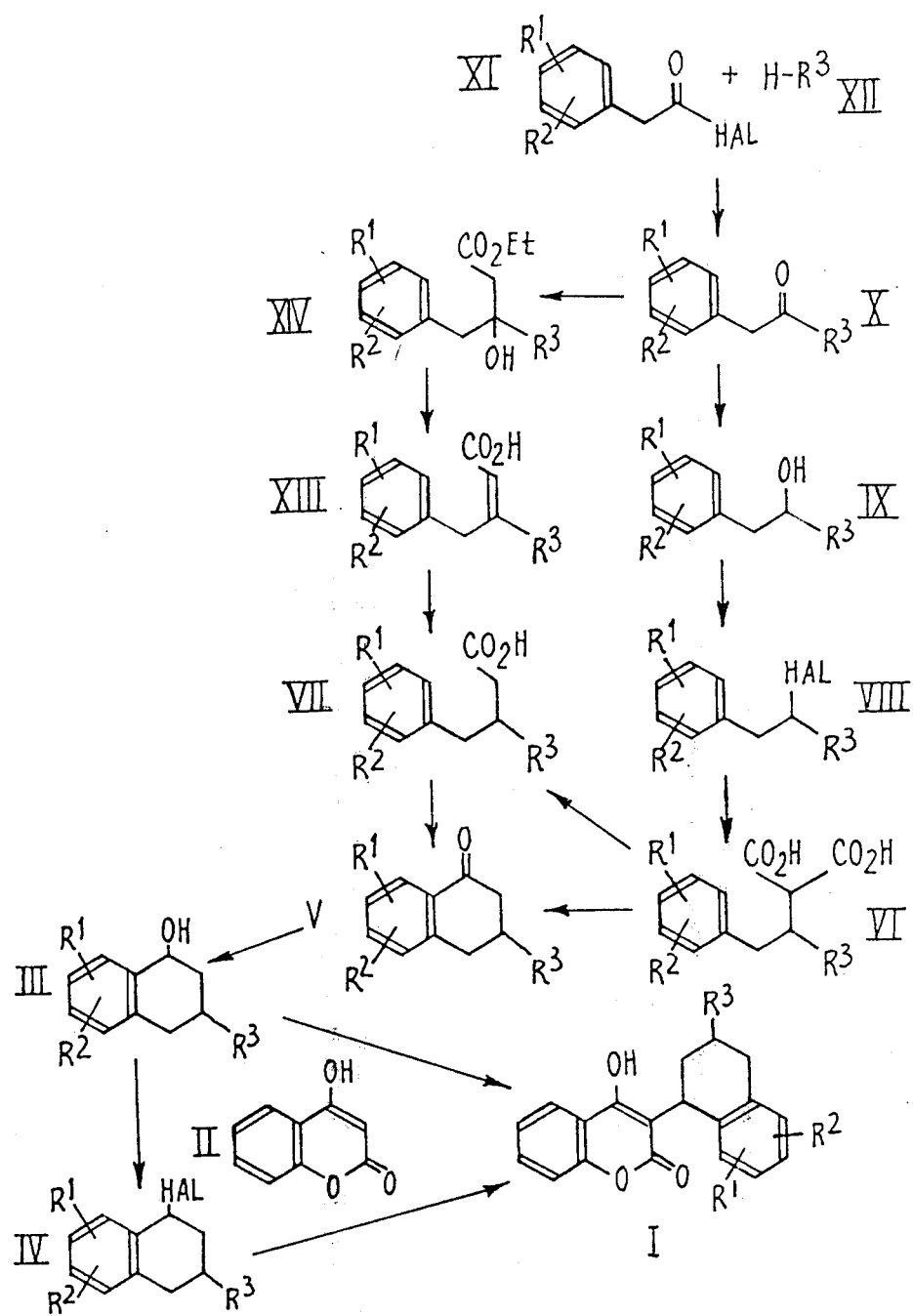

4-HYDROXYCOUMARIN COMPOUNDS USEFUL AS ANTICOAGULANT RODENTICIDES

This Application is a Divisional of our copending application Ser. No. 473,161 Filed May 22, 1974 now U.S. Pat. No. 3,957,824.

This invention relates to compounds of general formula I having anticoagulant properties, which are useful as rodenticides or in human medicine.

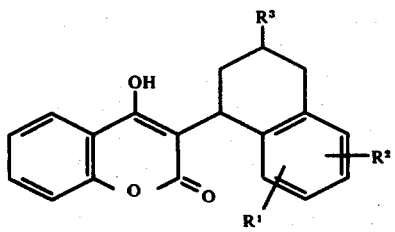

Where $R^1$ and $R^2$ are the same or different and are hydrogen or halogen atoms, preferably chlorine or bromine, or alkyl or alkoxy groups, preferably having up to 6 carbon atoms, $R^3$ is an aryl group having the formula

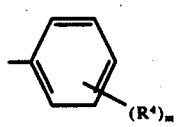

where m is 1 or 2, and $R^4$ is the same or different and is a halogen atom, a straight or branched chain alkyl or alkoxy group, preferably containing at least 2, more preferably from 5 to 12 carbon atoms, a cycloalkyl, preferably cyclohexyl group, an aralkyl, preferably α-aralkyl group, a phenyl or a phenoxy group, or a halogeno, preferably para halogeno, substituted derivative thereof. The halogen atom or atoms are preferably chlorine or bromine. Where n is 1, $R^4$ is preferably in the para position and when m is 2 one of the $R^4$ groups is preferably in the pure position. Preferably $R^3$ contains at least 1 but not more than 3 and optimally not more than 2 halogen atoms.

Compounds of general formula I may be prepared by condensing 4-hydroxy coumarin (II) with compounds of general formula III without a solvent or in a solvent such as acetic acid in the presence of a dehydrating agent such as sulphuric acid or by condensing 4-hydroxy coumarin (II) with a compound of general formula IV with or without the use of a solvent.

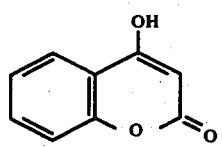

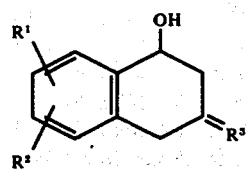

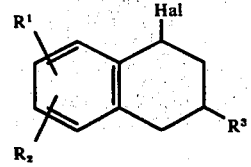

$R^1$, $R^2$ and $R^3$ have the meanings given previously and Hal is halogen, preferably chlorine or bromine.

Compounds of structure IV may be prepared from compounds of general structure III by treatment with reagents such as phosphorus tribromide, phosphorus trichloride or thionyl chloride in an inert solvent such as methylene chloride, chloroform or carbon tetrachloride, Compounds of general formula III may be prepared by reduction of compounds of general formula V with for example hydrogen in the presence of a catalyst, sodium borohydride in a solvent such as methanol or ethanol, aluminium isopropoxide in isopropanol or by any other means commonly used for the reduction of ketones to alcohols.

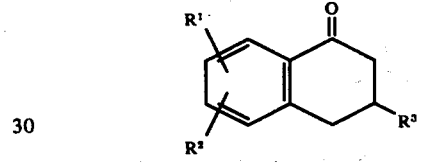

in which $R^1$, $R^2$ and $R^3$ have the meanings given previously.

Compounds of general formula V may be prepared by treatment of compounds of general formula VI or VII with a condensing agent such as polyphosphoric acid.

In the case of cyclisation of compounds of general formula VI an elevated temperature is necessary so that decarboxylation occurs.

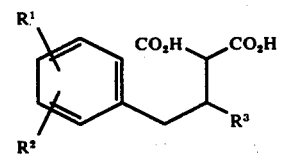

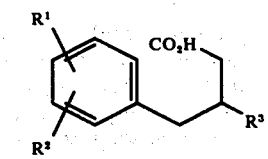

in which $R^1$, $R^2$ and $R^3$ have the meanings previously given.

Compounds of general formula VI or VII may be prepared by treating a salt of a malonic ester derivative, such as the sodium salt of diethyl malonate, in a solvent such as methanol or ethanol or dimethyl formamide with a compound of general formula VIII, followed by hydrolysis with for example sodium or potassium hydroxide in aqueous ethanol or hydrochloric or sulphuric acid. Compounds of general formula VII may be prepared from compounds of general formula VI by heating at or near the melting point. Compounds of general formula VI or VII may also be prepared from compounds of general formula VIII by other methods commonly used for the conversion of Hal in formula VIII into a $CH_2CO_2H$ or $CH(CO_2H)_2$ group or from compounds of general formula X by methods commonly used for the conversion of ketones into acetic acid derivatives with the addition of two carbon atoms.

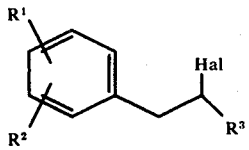

VIII in which $R^1$, $R^2$, $R^3$ and Hal have the meanings given previously.

Compounds of general formula VIII may be prepared by treatment of compounds of general formula IX with for example phosphorus tribromide, phosphorus trichloride or thionyl chloride in an inert solvent such as methylene chloride, chloroform or carbon tetrachloride.

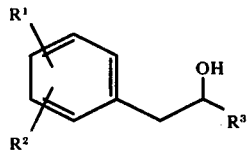

IX in which $R^1$, $R^2$, $R^3$ have the meanings given previously.

Compounds of general formula IX may be prepared by the reduction of compounds of general formula X with for example sodium borohydride in a solvent such as ethanol or methanol, aluminium isopropoxide in isopropanol (a Meerwein-Ponndorf reduction) hydrogen in the presence of a catalyst, or by such other methods as are commonly used for the reduction of ketones to alcohols.

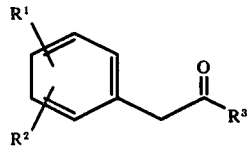

X in which $R^1$, $R^2$ and $R^3$ have the meanings previously.

Compounds of the general formula VII may also be prepared by the reduction of compounds of the general formula XIII. The reduction may conveniently be effected by catalytic hydrogenation, e.g. by gaseous $H_2$ over platinum oxide catalyst in solution in acetic acid. Other well known techniques of reduction of a double bond may also be employed as appropriate.

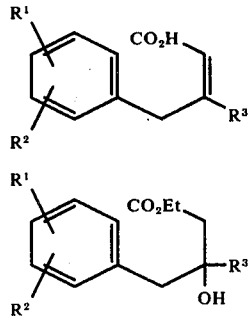

in which $R^1$, $R^2$, $R^3$ have the meanings previously given.

Compounds of the general formula XIII may be prepared from compounds of the general formula XIV (or the free acid) by dehydration and, if necessary, hydrolysis of the ester. Conveniently this can be done by treating compounds of the general formula XIV with toluene sulphonic acid in toluene to dehydrate, e.g. under a Dean-Stark apparatus, and then hydrolysing the ester in aqueous, ethanolic alkali (e.g. NaOH) and distilling off the ethanol.

Compounds of the general formula XIV may be prepared by treating compounds of the general formula X in solution with zinc and a halogeno acetic acid ester, e.g. ethyl bromoacetate, followed by hydrolysis of the product. A suitable solvent is benzene and the reaction is conveniently carried out at elevated temperature, e.g. under reflux. The product may conveniently be hydrolysed by addition of dilute mineral acid and isolation of the compound of the general formula XIV from the benzene layer. Compounds of the general formula XIV may also be prepared from compounds of the general formula X by other methods commonly used for the conversion of ketones to β-hydroxy acetic acid derivatives with the addition of two carbon atoms. Compounds of general formula X may be prepared by the Friedel-Crafts condensation of a compound of general formula XI with a compound of general formula XII in the presence of a Lewis Acid such as aluminium chloride in an inert solvent such as methylene chloride or carbon disulphide.

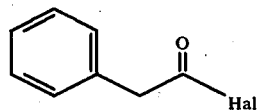

XI

H—$R^3$  XII in which $R^1$, $R^2$, $R^3$ and Hal have the meanings given previously.

The synthetic routes described above are illustrated in the outline reaction sequence shown in the accompanying drawings.

The compounds with which this invention is concerned can exist as both cis and trans isomers. Compounds obtained by the methods described above show two spots on t.l.c., and we surmise that they are produced as a mixture of the cis and trans isomers. We have now separated the two isomers (see Examples 1 and 8) but we have not yet identified which is cis and which is trans. Further the compounds of the invention used in the trials described below were not entirely pure and so the results given may differ somewhat from those achieved with pure materials.

The position of the substituents $R^1$ and $R^2$ in the phenyl ring of the tetrahydronaphthalene group is not believed to be critical with respect to the anticoagulant activity of the products. However, clearly, using the synthetic route described, some of the substituted phenylacetic acids used as starting materials will produce intermediate tetralones in more than one isomeric form. This is a disadvantage from the point of view of the synthesis of pure compounds but it is believed that it would be possible to use final products made from mixtures of such isomers as anticoagulants. Among mono-substituted phenylacetic acids (i.e. when either $R^1$ or $R^2$ but not both is hydrogen) ortho- and para-forms produce only one tetralone whereas meta-forms produce two, the 6-, and the 8-substituted. Among di-substituted phenyl acetic acids the 2,3-, 2,4- and 2,5-forms produce only one corresponding tetralone whereas the 3,4- 3,5- and 4,5- forms can produce corresponding pairs of isomers. Mixed tetralone intermediates will, of course, produce mixed tetrahydro-naphthalene systems in the final products. From a practical point of view para-substituted phenylacetic acids are the most readily available commercially, ortho-forms are rather less readily available and meta-forms rather difficult to obtain. Thus para-substituted and 2,4-disubstituted phenylacetic acids are preferred, because of their more ready availability, in the process of the present invention.

The following Examples illustrate preparation of compounds according to the invention.

EXAMPLE 1

3-(3-p-Biphenyl-1,2,3,4-tetrahydronaphth-1-yl-4-hydroxy coumarin

A. α-Benzyl-p-phenylbenzyl alcohol:

i. Sodium borohydrite (6.7g) was added to a suspension of benzyl-p-diphenyl ketone (47.4g) in ethanol (150 ml). The solution was heated to boiling, the heat removed and the solution stirred for 1 hour. The mixture was diluted with water and extracted with chloroform. The chloroform was evaporated and the residue collected with petroleum ether (b.p. 40°–60°) to give 46.7g; m.p. 107°–108°.

(Found: C,87.7; H,6.3 $C_{20}H_{18}O$ requires: C,87.6; H,6.6%)

ii. Benzyl p-biphenyl ketone (41.6g aluminium isopropoxide (40g) and isopropanol (200 ml) were heated to boiling and the acetone/isopropanol distilled out (120 ml of distillate was collected in 4 hours). The mixture was cooled, decomposed by the addition of hydrochloric acid plus water and extracted with methylene chloride. The methylene chloride was washed (H$_2$O), dried (MgSO$_4$) and evaporated to give 39.9g; m.p. 105°–107°.

B. α-Benzyl-p-phenylbenzyl bromide and α-Benzyl-p-phenyl benzyl chloride i. Phosphorus tribromide (7 ml) was added dropwise with stirring to a solution of α-Benzyl-p-phenyl benzyl alcohol (41.7g) in methylene chloride (150 ml). After 3 hours the mixture was added to water, the methylene chloride separated off, washed (H$_2$O) and evaporated. The residue was recrystallized from petroleum ether (b.p. 80°–100°) to give 46.1g; m.p. 99°–100°.

(Found: C,71.6; H,5.35 $C_{20}H_{17}Br$ required: C,71.2; H,5.1%)

ii. Similarly using thionyl chloride (2.9 ml) α-benzyl-p-phenyl benzyl alcohol (10g) and methylene chloride (50 ml) there was obtained after recrystallizing from petroleum ether (b.p. 60°–80°) 9.5g; m.p. 89°–93°.

(Found: C,82.0; H,5.9 $C_{20}H_{17}Cl$ requires C,82.0; H,5.8%)

C. (1-p-Biphenyl-2-phenylethyl) malonic acid i. α-Benzyl-p-phenyl benzyl bromide (16.8g) was added to a solution of the sodium salt of diethyl malonate (prepared from 7.7 ml of diethyl malonate and 2.0g of 60% sodium hydride) in dimethylformamide (40 ml). The solution was stirred and heated at 97° for 16 hours, cooled and then diluted with methylene chloride and water. The mixture was filtered and the methylene chloride washed (H$_2$O) and evaporated. Sodium hydroxide (15g) water (100 ml) and ethanol (100 ml) were added to the residue and the mixture heated on a steam bath for 3 hours the ethanol being distilled off. The solution was filtered and the insoluble material washed with water. The filtrate was acidified and extracted with ethyl acetate. The ethyl acetate was evaporated and the residue collected with petroleum ether (b.p. 40°–60°) to give 11.4g, m.p. 186°–189° dec. A sample recrystallized from ethyl acetate had a m.p. 199°–201° dec.

(Found: C,76.4; H,5.4 $C_{23}H_{20}O_4$ requires C,76.65; H,5.6%)

ii. In a similar manner using α-benzyl-p-phenylbenzyl chloride (9.0g) 60% sodium hydride (1.31g), diethyl malonate (5-ml) and dimethyl formamide (26 ml) was obtained 2.1g., m.p. 190°–195° dec.

D. 3-p-Biphenyl tetralin-1-one i. (1-p-Biphenyl-2-phenylethyl) malonic acid 93.5g) and polyphosphoric acid (500g) were heated to 160° for 1 hour. Ice and methylene chloride were added to the mixture which was stirred until dissolved. The methylene chloride was separated off, passed through an alumina column which was eluted with methylene chloride. The methylene chloride was evaporated and the residue collected with petroleum ether to give 61.8g: m.p. 75°–77°. A sample recrystallised from petroleum ether (b.p. 80°–100°) had a m.p. 92°–94°.

(Found: C,88.3; H,6.3 $C_{22}H_{18}O$ requires: C,88.6; H,6.1%)

ii. (1-p-Biphenyl-2-phenylethyl) malonic acid (10.0g) was melted (temperature 200°). After cooling the residue was dissolved in water (300 ml) plus ammonia (30 ml) at 90°. The solution was filtered, acidified and extracted three times with chloroform. The chloroform was evaporated and the residue collected with petroleum ether (b.p. 40°–60°) to give 3-p-biphenyl-4-phenylbutyric acid (8.7g) m.p. 175°–178°. A sample recrystallised from ethanol had a m.p. 177°–179°.

(Found: C,82.9; H,6.2 $C_{22}H_{20}O_2$ requires: C,83.5; H,6.4%)

3-p-diphenyl-4-phenylbutyric acid (7.7g) and polyphosphoric acid (35g) were heated for 30 minutes at 160° and 30 minutes at 190° and the reaction mixture worked up as described in (i) to give on recrystallising from petroleum ether (b.p. 80°–100°) 4.3g; m.p. 92°–94°.

E. 3-p-Biphenyl tetralin-1-ol i. Sodium borohydride (8.4g) was added portionwise with stirring over 15 mins to a suspension of 3-p-diphenyl tetralin-1-one (65.8g) in ethanol (200 ml). The mixture was heated to 60° stirred for 30 minutes and diluted with water. The mixture was extracted three times with chloroform, and the chloroform washed (H$_2$O), evaporated and the residue collected with petroleum ether (b.p. 40°–60°) to give 62.4g; m.p. 145°–150°.

A sample purified by chromatography on silica using methylene chloride as an eluant and then recrystallising from ethanol had a m.p. 159°.

(Found: C,87.7; H,7.0 $C_{22}H_{20}O$ requires: C,88.0; H,6.7%)

ii. 3-p-Biphenyl tetralin-1-one (13.5g) isopropanol (60 ml) and aluminium isopropoxide (12g) were heated to boiling and the acetone/isopropanol distilled out (31 ml of distillate was collected over one hour). After cooling hydrochloric acid (14 ml) plus water (57 ml) was added and the solid filtered off and washed with water, 11.3g; m.p. 131°–139°.

A sample purified by chromatography on silica using methylene chloride as an eluant and then recrystallising from ethanol had a m.p. 145°.

The products obtained above may be isomeric or mixtures of isomers (cis and trans) but either product may be used in the subsequent reaction with 4-hydroxycoumarin.

F. 3-(3-p-Biphenyl-1,2,3,4-tetrahydronaphth-1-yl)-4-hydroxy coumarin i. Sulphuric acid (0.5 ml; 60° Be) was added to a mixture of 4-hydroxy coumarin (4.8g), 3-p- Biphenyl tetralin-1-ol (9.0 gms; obtained by sodium borohydride reduction) and acetic acid (15 ml) at 110°. The mixture was stirred and heated at 110° for 1 hour, then diluted with water and extracted twice with ether. The ether was extracted three times with dilute sodium hydroxide solution and the combined alkaline extracts acidified and extracted three times with chloroform. The chloroform was evaporated to a small volume and applied to a silica column which was eluted with chloroform. The fractions containing two components having Rf values of 0.45 and 0.55 were evaporated and the residue crystallised from ethyl acetate to give 3.75 gms; m.p. 210°–215°. Recrystallisation gave material of m.p. 215°–217°.

(Found: C,83.5; H,5.4. $C_{31}H_{24}O_3$ requires: C,83.8; H,5.4%)

ii. 4-Hydroxycoumarin (1.6g) and 3-p-biphenyltetralin-1-ol (3g; obtained by sodium borohydride reduction) were heated at 160° for 1 hour. The mixture was extracted with ether and then worked up as described in (i) to give 0.9 gms; m.p. 211°–212°.

iii. Phosphorus tribromide (0.7 ml) was added dropwise with stirring to a suspension of 3-p-diphenyltetralin-1-ol (m.p. 159°; 6.0g, prepared by sodium borohydride reduction) in methylene chloride (50 ml) the temperature being kept below 0°. After stirring for 1 hour the mixture was washed ($H_2O$) dried ($MgSO_4$) evaporated and the residue chromatographed on silica using benzene. The benzene was evaporated and the residue recrystallised from petroleum ether (b.p. 80°–100°) to give 1-bromo-3-p-diphenyltetralin (5.0g; 70%) m.p. 132° dec.

1-Bromo-3-p-diphenyltetralin (3.6g) and 4-hydroxycoumarin (1.6g) were heated at 130°–135° for thirty minutes. The residue was stirred with benzene (25 ml) the insoluble material filtered off and filtrate evaporated to give a solid which was collected with petroleum ether (b.p. 60°–80°) to give 3.5g: m.p. 202°–208°.

iv. 4-Hydroxycoumarin (14.4g) 3-p-diphenyltetralin-1-ol (27.0g; prepared by aluminium isopropoxide reduction) and acetic acid (45 ml) were heated to 105° and 80% sulphuric acid (1.5 ml) added over 3 minutes with stirring. After stirring at 110° for 1 hour, water (100 ml) was added and the mixture extracted with chloroform (100 ml) some insoluble material being rejected. The chloroform solution was chromatographed through alumina which was eluted with chloroform and the chloroform evaporated. The residue was extracted with hot hexane (150 ml) and the insoluble residue dissolved in hot toluene (any insoluble material being rejected) and hexane (200 ml) added to give 13.2g; m.p. 213°–216°.

The products obtained in Example 1 F(i) (ii) (iii) and (iv) are mixtures of two isomers as indicated by t.l.c. having Rf values of 0.18 and 0.24 (benzene/silica). These isomers may be separated by preparative t.l.c. on silica the plates being run several times with benzene, or by column chromatography on silica using benzene as an eluant.

The slower-running isomer was obtained by crystallising from ethyl acetate m.p. 227°–229°. The faster-running isomer was obtained by crystallising from ethyl acetate m.p. 200°–202°.

The products obtained in Example 1 F (i) (ii) and (iv) contain the two isomers in approximately equal proportions, whereas the product obtained in Example 1F (iii) contains the slow-running isomer and the fast-running isomer in the approximate ratio of 5:1.

EXAMPLE 2

An alternative method to that described in Example 1 may be used for conversion of benzyl p-diphenyl ketone into 3-p-biphenyl-4-phenyl butyric acid:

A. Ethyl-3-p-biphenyl-3-hydroxy butyrate

Benzyl p-biphenyl ketone (10g), zinc dust (3.7g) and benzene were stirred and heated at 80° and ethyl bromoacetate (8.6g) in benzene (20 ml) added dropwise. After stirring and heating 3 hours the mixture was left 16 hours and then decomposed by the addition of 2N sulphuric acid (100 ml). The benzene was separated, washed ($NaHCO_3$) and evaporated to give a residue which was recrystallised from petroleum ether to give 11.2g, m.p. 95°–97°.

(Found: C,80.1; H,6.7. $C_{24}H_{24}O_3$ requires: C,80.0; H,6.7%)

B. 3-Benzyl-3-p-biphenylacrylic acid

Ethyl 3-p-biphenyl-3-hydroxy-4-phenylbutyrate (5g) toluene sulphonic acid (0.1g) and toluene (100 ml) were heated under reflux 3 hours water being removed using a Dean-Stark apparatus. The solution was evaporated, sodium hydroxide (3.0g), water (30 ml) and ethanol (30 ml) added to the residue and the mixture heated on a steam bath for 2 hours, the ethanol being distilled off. Water (100 ml) was added and the solution extracted with ether. The aqueous layer was acidified, extracted twice with ethyl acetate and the ethyl acetate dried ($MgSO_4$) and evaporated. The residue was collected with petroleum ether (b.p. 40°–60°) to give 4.24g, m.p. 165°–174°. A sample recrystallised from toluene had a m.p. 170°–178°.

3-p-Biphenyl-4-phenylbutyric acid

3-Benzyl-3-p-biphenyl acrylic acid (5.0g), acetic acid (100 ml) and platinum oxide (0.3g) were shaken in an atmosphere of hydrogen at NTP for 4 hours. The solution was filtered and evaporated and the residue recrystallised from ethanol to give 2.2g, m.p. 172°–173°.

The following table (Table 1) gives details of compounds prepared by the synthetic routes described in Examples 1 and 2.

TABLE 1

| Ex. No. | | SUBSTITUENTS R¹ R² R³ | | | m.p.t. °C | ANALYSIS Experimental | | Theoretical | |
|---|---|---|---|---|---|---|---|---|---|
| | | | | | | C | H | C | H |
| 1 | i | | H | H | -⌬-⌬ (biphenyl) | 215–217 | 83.5 | 5.4 | 83.8 | 5.4 |
| | ii | | | | | 211–212 | | | | |
| | iii | | | | | 202–208 | | | | |
| | iv | | | | | 213–216 | | | | |
| 3 | | Cl(7) | H | | -⌬-⌬ | 255–256 | 77.4 | 4.75 | 77.3 | 4.8 |
| 4 | | H | H | | -⌬-O-⌬ | 200–201 | 80.45 | 5.2 | 80.85 | 5.25 |
| 5 | | H | H | | -⌬-⌬-Br | 228–230 | 71.1 | 4.4 | 71.2 | 4.4 |
| 6 | | Me(7) | H | | -⌬-⌬ | 230–232 | 83.7 | 5.8 | 83.8 | 5.7 |
| 7 | | H | H | | -⌬-Cl | 115–130 | 74.3 | 5.2 | 74.5 | 5.2 |
| 8 | i | H | H | | -⌬-⌬-Cl | 222–225 | 77.5 | 5.0 | 77.8 | 4.8 |
| | ii | | | | | 228–230 | 77.5 | 5.0 | | |
| | iii | | | | | 235–237 | 77.6 | 5.1 | | |
| | iv | | | | | 233–234 | 77.8 | 4.9 | | |
| 9 | | H | H | | -⌬-Br | 210–213 | 67.3 | 4.2 | 67.2 | 4.3 |
| 10 | | H | H | | -⌬-O-⌬-Br | 199–201 | 69.1 | 4.0 | 69.1 | 4.3 |
| 11 | | H | H | | -⌬-⬡ (cyclohexyl) | 170–174 | 82.9 | 6.8 | 82.6 | 6.7 |
| 12 | | H | H | | -⌬-CH₂-⌬ | 75–85 | 83.6 | 5.9 | 83.8 | 5.7 |
| 13 | | H | H | | -⌬-nC₆H₁₃ | 109–111 | 82.4 | 7.1 | 82.3 | 7.1 |

Examples 3, 4, 5, 6, 7, 8, 10, 11, 12, 13 were made by the route described in Example 1F (ii) Examples 9 and 13 were made by the route described in Example 1F (iii).

In Example 8 the product from the direct condensation of 3-(4'-Chloro-4-bi-phenyl) tetralin-1-ol and 4-hydroxycoumarin was chromatographed on silica using chloroform as eluant and the fractions containing components having Rf values 0.8 and 0.71 collected and evaporated. The residue was rechromatographed on silica using chloroform/trichloroethylene (1:1) as eluant to give four fractions. The first fraction, (i), contained the component having an Rf value of 0.8, the next two fractions, (ii) and (iii), contained both components and the fourth fraction, (iv), contained the component having an Rf value of 0.71. The fractions were evaporated and the residue recrystallised from ethyl acetate to give the properties listed in the table.

PHARMACOLOGICAL PROPERTIES

The products of the invention have very high levels of anti-coagulant activity relative to that of commercially available compounds. More important is the activity of the materials against an anti-coagulant resistant strain of rats. The ratio of activity resistant: non-resistant is far smaller than that seen in other compounds, i.e. there is little resistance to the compounds of the invention.

We believe that the increased activity of the compounds of the invention to resistant rats is due to a high level of affinity between the particular stereochemical configuration of these materials and the receptor site of the modified resistant enzyme.

RESULTS OF TRIALS

The results shown below were obtained by the following methods:

1. Prothrombins: Male rats were used throughout.

The anti-coagulants were injected by the intraperitoneal route at the same time on three consecutive days. The solvent used was polyethylene glycol 300.

F.F.G.M. laboratory pellets (compounded rat food used in animal houses) and tap water were available throughout the treatment period.

Prothrombin times were determined 24 hours after the last injection by the one stage method of Quick.

E.D. 50s were estimated by calculating the percentage extension of prothrombin time, plotting results upon logarithmic probability sheets and drawing the best line of fit. The E.D. 50 in this case, is the dose of anti-coagulant required to prolong the prothrombin times by 50%.

2. Baits: Baits containing 0.025 or 0.020% anti-coagulant were produced by acetone slurry. After air drying, these were diluted as necessary by hand mixing. The bait base in all cases was medium grade stabilized oatmeal.

The prepared baits were offered to rats or mice. No alternative diet was available. Tap water was available ad lib. Baits were replaced daily. Mortality counts were made daily up to 10 days of continuous feeding.

1 Prothrombin

Prothrombin ED 50* 4th day after 3 daily I.P. inections in PEG 300.
Approximate ED 50 mg/Kg/Day × 3 daily doses
Male *Rattus norvegious*

TABLE 2

| Compound | Homozygous Resistant | Wistar | Resistance Factor**Warfarin |
|---|---|---|---|
| Warfarin S(−) | > 50 | 0.35 | > 100 |
| Warfarin R(+) | > 50 | 3.50 | > 15 |
| Coumatetralyl | ≃ 5.0 | ~ 16 | |
| Chlorophacinone | ≃ 20 | 0.19 | ~ 100 |
| Diphacinone | > 20 | 0.23 | > |
| Pival | > — | — | |
| 1 i | 0.4 | 0.15 | 2.7 |
| 1 iii | 0.32 | 0.15 | 2.1 |
| 1 iv | 0.32 | 0.17 | 1.9 |
| 3 | 0.45 | 0.25 | 1.8 |
| 4 | 0.12 | 0.12 | 1.0 |
| 5 | 0.10 | 0.08 | 1.3 |
| 6 | 0.40 | 0.18 | 2.2 |
| 7 | 0.14 | 0.09 | 1.6 |
| 8 i | — | 0.12 | — |
| 8 ii + iii | 0.12 | 0.10 | 1.2 |
| 8 iv | — | 0.07 | — |
| 9 | 0.22 | 0.13 | 1.7 |
| 10 | 0.07 | 0.07 | 1.0 |
| 11 | — | 0.33 | — |
| 12 | — | 0.18 | — |
| 13 | — | 0.20 | — |

**E.D. 50 Resistant/E.D. 50 Non-Resistant

| | Resistant | Normal |
|---|---|---|
| Activity of product of Example 1 i relative to S(−) Warfarine | > 100 X | 2 |
| Activity of product of Example 1 i relative to Coumatetralyl: | > 10 X | 2 |

2. Bait Trials 10 day continuous exposure; no choice
a. Resistant female homozygous resistant *R. norvegious*.

TABLE 3

| Compound | Concentration (ppm) | Mortality | |
|---|---|---|---|
| Warfarin | 250 | 0/10 | |
| Chlorophacinone | 250 | 0/5 | Standards |
| Coumatetralyl | 250 | 1/5 | |
| | 200 | 1/5 | |
| 1 i | 20 | 5/5 | |
| | 10 | 7/10 | |
| | 5 | 0/15 | |
| 4 | 10 | 4/5 | |
| | 5 | 3/10 | |
| 5 | 10 | 5/5 | |
| | 5 | 5/5 | |
| | 2 | 4/5 | |
| 6 | 50 | 5/5 | |
| | 10 | 0/5 | |
| 7 | 5 | 10/10 | |
| | 2 | 0/5 | |
| 8 ii + iii | 5 | 5/5 | |
| | 2 | 5/5 | |
| | 1 | 5/5 | |
| 9 | .5 | 5/5 | |
| | 2 | 3/5 | |
| 10 | 5 | 5/5 | |
| | 1 | 2/5 | |
| 11 | 50 | 5/5 | |
| 12 | 10 | 4/5 | |
| 13 | 10 | 1/5 | | b. Non-resistant LAC mice

| Compound | Concentration ppm | Mortality |
|---|---|---|
| S(−) Warfarin | 20 | 10/10 |
| | 10 | 5/10 |
| | 5 | 2/10 |
| R(+) Warfarin | 100 | 9/10 |
| | 20 | 1/10 |
| | 10 | 0/10 |
| 1 i | 1.0 | 10/10 |
| | 0.5 | 15/20 |
| | 0.2 | 0/10 |
| 4 | 0.5 | 5/10 |
| 5 | 0.5 | 9/10 |
| 6 | 2.0 | 10/10 |
| 7 | 1.0 | 10/10 |
| 8 ii + iii | 0.5 | 10/10 |
| 9 | 0.5 | 9/10 |
| 10 | 0.5 | 10/10 |
| | 0.2 | 0/10 | c. Resistant *Rattus rattus*

| Compound | Concentration ppm | Mortality |
|---|---|---|
| Warfarin | 250 | 0/5 |
| 1 i | 50 | 5/5 |
| 8 ii | 50 | 5/5 | d. Resistant *Mus. musculis*

| Compound | Concentration ppm | Mortality |
|---|---|---|
| Warfarin | 250 | 0/5 |
| 1 i | 50 | 5/5 |
| 8 ii + iii | 50 | 5/5 |

3. Activity of isomers

One stage prothrombin times as measured on the fourth day after
3 daily I.P. injections
Male *R. norvegious* used throughout.

| | Dose mg/Kg/day × 3 | Mean Prothrombin seconds |
|---|---|---|
| 1 fast-running isomer | 0.3 | 213 |
| Wistar rats | 0.15 | 126 |
| | 0.08 | 15 |
| 1 fast-running isomer Homozygous resistant rats | 0.4 | 24.9 |
| 1 slow-running isomer | 0.15 | 190.5 |
| Wistar rats | 0.10 | 130.0 |
| 1 slow-running isomer Homozygous resistant rats | 0.4 | 212 |
| | 0.2 | 128.3 |
| | 0.1 | 28.0 |
| 8 fast-running isomers(i) | 0.2 | 212+ |
| Wistar rats | 0.1 | 83.4 |
| | 0.075 | 40.2 |
| 8 slow-running isomers(iv) | 0.10 | 212+ |
| Wistar rats | 0.05 | 73.5 |
| | 0.02 | 16.7 |

We claim:
1. A rodenticidal composition comprising a carrier in combination with, as active ingredient, a rodenticidally effective amount of a compound of the formula

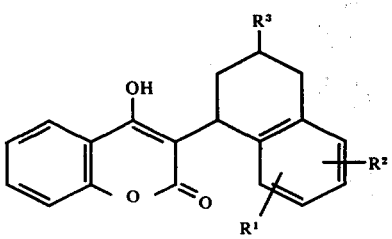

wherein
R¹ and R² are independently selected from the group consisting of hydrogen, halogen, alkyl of up to 6 carbon atoms and alkoxy of up to 6 carbon atoms, and
R³ is an aryl group of the formula

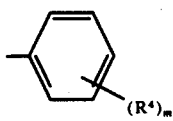

where
m is 1 or 2, and
each R⁴ is independently selected from the group consisting of halogen alkyl of 2–12 carbon atoms, alkoxy of 2–12 carbon atoms, cyclohexyl, benzyl, phenyl, halogenophenyl, phenoxy and halogenophenoxy, provided that R³ contains not more than 3 halogen atoms.

2. The composition as claimed in claim 1 wherein the amount of the compound is at least 1 part per million by weight of the composition.

3. The composition as claimed in claim 2 wherein the amount of the compound is from 5 to 50 parts per million by weight of the composition.

4. The composition as claimed in claim 1 wherein the active ingredient is 3-(3-p-biphenyl-1,2,3,4-tetrahydronaphth-1-yl)-4-hydroxycoumarin.

5. The composition as claimed in claim 1 wherein the active ingredient is 3-(3-p-chlorophenyl-1,2,3,4-tetrahydronaphth-1-yl)-4-hydroxycoumarin.

6. The composition as claimed in claim 1 wherein the active ingredient is 3[3-(4'-chloro-4-biphenyl)-1,2,3,4-tetrahydronaphth-1-yl]-4-hydroxycoumarin.

7. The composition as claimed in claim 1 wherein the active ingredient is 3-[3-(4'-bromo-4-biphenyl)-1,2,3,4-tetrahydronaphth-1-yl]-4-hydroxycoumarin.

8. The composition as claimed in claim 1 wherein the active ingredient is 3-[3-p-(4-bromophenoxy)-phenyl-1,2,3,4-tetrahydronaphth-1-yl]-4-hydroxycoumarin.

9. A method of killing rodents comprising feeding the rodents a rodenticidally effective amount of the composition as claimed in claim 1.

10. The method as claimed in claim 9 wherein the active ingredient is 3-(3-p-biphenyl-1,2,3,4-tetrahydronaphth-1-yl)-4-hydroxycoumarin.

11. The method as claimed in claim 9 wherein the active ingredient is 3-(3-p-chlorophenyl-1,2,3,4-tetrahydronaphth-1-yl)-4-hydroxycoumarin.

12. The method as claimed in claim 9 wherein the active ingredient is 3-[3-(4'-chloro-4-biphenyl)-1,2,3,4-tetrahydronaphth-1-yl]-4-hydroxycoumarin.

13. The method as claimed in claim 9 wherein the active ingredient is 3-[3-(4'-bromo-4-biphenyl)-1,2,3,4-tetrahydronaphth-1-yl]-4-hydroxycoumarin.

14. The method as claimed in claim 9 wherein the active ingredient is 3-[3-p-(4-bromophenoxy)-phenyl-1,2,3,4-tetrahydronaphth-1-yl]-4-hydroxycoumarin.

* * * * *